United States Patent [19]

Wright

[11] 3,965,199

[45] June 22, 1976

[54] HYDROGENATION AND HYDROGENOLYSIS OF CARBOHYDRATES WITH TUNGSTEN OXIDE PROMOTED SUPPORTED NICKEL CATALYST

[75] Inventor: Leon W. Wright, Wilmington, Del.

[73] Assignee: ICI United States Inc., Wilmington, Del.

[22] Filed: May 10, 1974

[21] Appl. No.: 468,763

Related U.S. Application Data

[60] Continuation of Ser. No. 247,689, April 26, 1972, abandoned, which is a division of Ser. No. 9,059, Feb. 5, 1970, Pat. No. 3,691,100.

[52] U.S. Cl. ............................................. 260/635 C
[51] Int. Cl.² ............................................. C07C 29/00
[58] Field of Search .................................. 260/635 C

[56] References Cited
UNITED STATES PATENTS

| | | | |
|---|---|---|---|
| 1,990,245 | 2/1935 | Mueller et al. | 260/635 C |
| 2,325,206 | 7/1943 | Stengel | 260/635 C |
| 2,518,235 | 8/1950 | Harstra et al. | 260/635 C |
| 2,759,023 | 8/1956 | Kool et al. | 260/635 C |
| 3,396,199 | 8/1968 | Kasehagen | 260/635 C |
| 3,538,019 | 11/1970 | Capik et al. | 260/635 C |
| 3,691,100 | 9/1972 | Wright | 260/635 C |

*Primary Examiner*—Joseph E. Evans

[57] ABSTRACT

Disclosed is a process for the production of polyhydric alcohols from carbohydrates. Also disclosed is a catalyst comprising finely divided metallic nickel and finely divided tungsten oxide supported on an inert carrier wherein the metallic nickel is from 15 to 45% by weight, based on total weight of catalyst, and wherein the tungsten oxide is from 0.5 to 16% by weight, based on the total weight of catalyst.

8 Claims, No Drawings

HYDROGENATION AND HYDROGENOLYSIS OF CARBOHYDRATES WITH TUNGSTEN OXIDE PROMOTED SUPPORTED NICKEL CATALYST

This is a continuation of application Ser. No. 247,689, filed Apr. 26, 1972, now abandoned, which in turn is a division of Ser. No. 9,059, filed Feb. 5, 1970, now U.S. Pat. No. 3,691,100.

The present invention relates to improved catalysts and to methods for the production of such catalysts. This invention further relates to an improved process for the production of polyhydric alcohols from carbohydrates. More particularly, this invention relates to tungsten oxide promoted supported nickel catalysts which are useful for the production of polyhydric alcohols from carbohydrates.

The term "hydrogenation" as used throughout the specification and appended claims includes the addition of hydrogen to chemical compounds.

The term "hydrogenolysis" as used throughout the specification and appended claims includes the cracking of the carbon to carbon linkage of a molecule and the addition of hydrogen to each of the fragments produced by the cracking.

The term "carbohydrate" as used throughout the specification and appended claims includes monosaccharides and polysaccharides.

The term "polysaccharide" as used throughout the specification and appended claims includes those saccharides containing more than one monosccharide unit.

A wide variety of catalysts have been proposed for the preparation of polyhydric alcohols from carbohydrates. The catalysts most often used for this purpose are the Raney nickel catalyst, such as those described in J.A.C.S., 54, pages 4116–4117, (1932) and in U.S. Pat. No. 2,983,734, and finally divided supported nickel catalysts, such as those disclosed in U.S. Pat. No. 2,749,371. These catalysts, however, have not been entirely satisfactory for a number of reasons. A serious disadvantage of these catalysts is that they are not effective for the preparation of polyhydric alcohols directly from polysaccharides in general. In the preparation of hexitols from polysaccharides with these catalysts, for example, it is usually necessary to first hydrolyze the polysaccharides to monosaccharides prior to hydrogenation. Moreover, in the preparation of mannitol and sorbitol from monosaccharides with these catalysts, a substantial amount of undesirable isomers such as iditol are formed. A further disadvantage of these catalysts is that they are not effective for the preparation of glycerine directly from monosaccharides. In the preparation of glycerine from monosaccharides with these catalysts, it is necessary to carry out the hydrogenation in the presence of a cracking agent, such as calcium oxide or calcium hydroxide. Thus these prior art catalysts are not effective as hydrogenolysis catalysts. Accordingly, there is a great need in the art for a catalyst which would be useful for the production of polyhydric alcohols such as glycerine and hexitols from monosaccharides and polysaccharides and which would not require the presence of a hydrolyzing agent or a cracking agent.

It is an object of this invention to provide a novel catalyst.

It is another object of this invention to provide a catalyst for the production of polyhydric alcohols from carbohydrates.

It is another object of this invention to provide a catalysts which is useful as either a hydrogenation catalyst or a hydrogenolysis catalyst.

It is another object of this invention to provide a catalyst which is highly effective for the production of polyhydric alcohols directly from polysaccharides.

It is an object of this invention to provide a process for the production of tungsten oxide promoted supported nickel catalysts.

It is another object of this invention to provide an improved process for the preparation of polyhydric alcohols from carbohydrates.

It is an object of this invention to provide a process for the preparation of hexitols directly from monosaccharides and/or polysaccharides.

It is an object of this invention to provide a process for the preparation of glycerine directly from monosaccharides and/or polysaccharides without the need for an additional cracking agent.

The foregoing objects and still further objects are accomplished according to the present invention by providing catalysts which comprise finely divided metallic nickel and finely divided tungsten oxide supported on an inert carrier wherein the amount of metallic nickel is from 15 to 45% by weight and the amount of tungsten in the form of tungsten oxide is from 0.5 to 16% by weight, based on the total weight of catalyst. In order to achieve the objects and advantages of this invention, it is essential that the catalysts contain amounts of metallic nickel, tungsten oxide, and inert carrier to furnish a nickel and tungsten content within the ranges defined above.

The inert carrier on which the finely divided metallic nickel and finely divided tungsten oxide are deposited may be any of the inert materials used heretofore for supporting hydrogenation catalysts. Illustrative examples of inert carriers or supports are diatomaceous earth, finely divided silica, kieselguhr, and activated carbon. A preferred carrier is diatomaceous earth, (e.g. Johns-Manville Hyflo Super Cel).

The catalyst of this invention may also contain small amounts of finely divided iron supported on the inert carrier. It has been found that small amounts of iron increase the activity of the catalyst. The amount of iron present in a catalyst may be up to 2.5%, preferably 0.1% to 2.0% by weight, based on the total weight of catalyst. The activity of the catalyst may be even further increased by the presence of up to 2.0% by weight, based on the total weight of catalyst, of finely divided copper, chromium, and/or cerium.

A preferred class of catalysts of this invention comprises finely divided metallic nickel and finely divided tungsten oxide supported on an inert carrier wherein the metallic nickel content is from 18 to 25% by weight and the tungsten content is from 2 to 12% by weight, based on the total weight of catalyst.

The catalyst of this invention may be prepared by forming a slurry of an inert carrier in an acidic, aqueous solution of nickel nitrate and ammonium tungstate [$(NH_4)_2WO_4$], neutralizing the slurry with an alkali metal carbonate to precipitate nickel carbonate, nickel hydroxide, and tungsten oxide onto the inert carrier, and reducing the nickel carbonate and nickel hydroxide to metallic nickel. $(NH_4)_2WO_4$ may be prepared by mixing $H_2WO_4$ with excess $NH_4OH$ on a steam bath.

Catalysts containing finely divided metallic iron, copper, chromium or cerium may be prepared by adding the nitrate of the metal to the slurry of inert carrier and aqueous solution of nickel nitrate and ammonium tungstate prior to the addition of the alkali metal carbonate. Catalysts containing finely divided nickel phosphate may be prepared by adding phosphoric acid to the slurry prior to neutralization. A preferred method of preparing the catalyst of this invention comprises: forming a slurry of inert carrier in an acidic, aqueous solution of nickel nitrate and ammonium tungstate; heating the slurry to 75° to 100°C.; adding alkali metal carbonate to the heated slurry to precipitate nickel carbonate, nickel hydroxide, and tungsten oxide onto the surface of the inert carrier, the nickel carbonate converting to nickel hydroxide due to the elevated temperature; and heating the catalyst to a temperature from 400°C. to 550°C. in the presence of hydrogen to reduce the nickel hydroxide to metallic nickel.

It has now been discovered that the hydrogenation of monosaccharides, the simultaneous hydrolysis and hydrogenation of polysaccharides, the hydrogenolysis of monosaccharides, and the simultaneous hydrolysis and hydrogenolysis of polysaccharides may be conducted in a practical and economical manner, substantially free of degradation and isomerization reactions, and with an almost substantially complete conversion of the monosaccharide and polysaccharide into polyhydric alcohol, by the novel method of incorporating the catalyst of this invention into an aqueous solution of carbohydrate and subjecting the mixture to the action of hydrogen under pressure at an elevated temperature.

The process of this invention may be broadly described as a method for the preparation of polyhydric alcohols from carbohydrates which comprises adding a small amount of a catalyst of this invention to an aqueous solution or suspension of a carbohydrate and treating the resulting mixture with hydrogen under a pressure of about 25 to about 200 atmospheres and a temperature of about 120°C. to about 250°C. until the conversion of the carbohydrate to polyhydric alcohol has been effected to the desired extent.

When the reaction is carried out at a temperature in the lower part of the recited temperature range, for example, 160°C., any polysaccharide present in the reaction mixture is hydrolyzed to its basic monosaccharide whose aldehyde or ketone groups are then hydrogenated to hydroxyl groups to produce the desired polyhydric alcohol of the monosaccharide. Those polysaccharides having free aldehyde or ketone groups in their molecular structure before they are subjected to the process of this invention may have these groups hydrogenated at the same time as the molecule is hydrolyzed. At any rate, both hydrolysis and hydrogenation reactions appear to be taking place simultaneously when polysaccharides are subjected to the process of the invention, and the reaction results in the polyhydric alcohols of the basic structural monosaccharides. Polysaccharides composed of different monosaccharides are hydrolyzed and hydrogenated to the polyhydric alcohol of the respective monosaccharides. Monosaccharides containing an aldehyde group are hydrogenated almost exclusively by the process of this invention to a polyhydric alcohol containing the same number of carbon atoms, the same space configuration of units attached to the carbon atoms, and with a hydroxyl group attached to the aldehyde carbon in place of the oxygen atom. Glucose, for example, is hydrogenated almost exclusively to sorbitol. Polysaccharides containing a ketone group in the molecule are hydrogenated to a mixture of approximately equal amounts of two different polyhydric alcohols due to the isometric nature of the ketone carbon atom. Both resulting polyhydric alcohols contain the same number of carbon atoms as the monosaccharide with the same space configuration of units attached to the carbon atoms, but one of the polyhydric alcohols has a hydroxyl group on one side of the ketone carbon atom in place of the oxygen atom, and the other polyhydric alcohol has the hydroxyl group on the opposite side of the ketone carbon atom in place of the oxygen atom. Fructose, for example has a ketone group at the second carbon atom and the molecule is hydrogenated to approximately equal amounts of sorbitol and mannitol.

When the process of this invention is carried out at a temperature in the upper part of the recited temperature range, for example, 220°C., any polysaccharide present in the starting material is hydrolyzed to its basic monosaccharide. Monosaccharide present in the reaction material is simultaneously cracked and hydrogenated to produce a hydrogenolysis reaction product which contains a high percent by weight of polyols having a shorter carbon chain length than the monosaccharide. The catalyst of the present invention is dual functional in that it contains both metallic sites for hydrogenation and acidic sites for cracking. Thus the catalyst of the present invention may be used for preparing polyols having a shorter chain length than the monosaccharide starting material. Furthermore, the catalyst of this invention does not require prior hydrolysis of any polysaccharides present in the starting material to monosaccharides or the presence of a cracking agent such as calcium oxide or calcium hydroxide. If desired, however, the process of this invention may be carried out in the presence of a cracking agent.

Illustrative examples of carbohydrates which may be converted to polyhydric alcohols in accordance with the process of this invention include, for example, glucose, fructose, galactose, mannose, altrose, allose, idose, gulose, arabinose, talose, ribose, xylose, sucrose, maltose, lactose, cellobiose, malibiose, invert sugar, wood sugar, starch and starch decomposition products such as dextrine, glucose syrups, and corn starch hydrolyzates. Mixtures of carbohydrates may also be used in the process of this invention.

The carbohydrate or mixture of carbohydrates to be subjected to the process of this invention are dissolved in water at the appropriate concentration. Concentrations of carbohydrates from 20% to about 80% by weight are usually employed for the reaction. Carbohydrate concentrations in the range of 40% to 70% by weight react particularly smoothly in the reaction and such concentrations are, therefore, the more preferred for this invention. It is not necessary for the carbohydrates to form true solutions with the water as suspensions and colloidal solutions of carbohydrates may be used.

The amount of catalyst to be used in the process of this invention may vary over a wide range and will depend upon the particular catalyst, carbohydrate, temperature and pressure which are employed in the process. In general, the higher the level of nickel and tungsten oxide in the catalyst and the higher the temperature and pressure used, the less catalyst is required. Polysaccharides tend to require a higher level of catalyst than do the monosaccharides. Catalyst concentrations sufficient to furnish from about 0.5% to about 3%, preferably from about 0.7% to about 2%, by weight of nickel based on the weight of carbohydrate are suitable. It will be understood, of course, that lower and higher concentrations of catalyst may be used if desired.

The process of the present invention is promoted by a positive hydrogen pressure and results generally improve as the pressure increases up to about 200 atmospheres. Above that pressure little improvement is shown, at least insufficient improvement to warrant the special apparatus which would be required. In general, pressures between about 75 atmospheres and about 150 atmospheres have been found to give the best results. The use of pressure below about 75 atmospheres probably would not be warranted in view of the better results which may be obtained in the preferred range. It is to be understood, however, that higher and lower pressures than those described above may be used when deemed necessary or desirable.

The reaction temperature range of the present process extends from about 120°C. to about 250°C. At temperatures lower than 120°C., the reaction is too slow to be practical. At temperatures higher than 250°C., charring of the starting carbohydrate may occur. The particular temperature used will depend mainly upon whether the desired product is a polyhydric alcohol containing a lower number of carbon atoms than the monosaccharidic unit of the starting carbohydrate, for example, the preparation of glycerine from a hexose, or a polyhydric alcohol containing the same number of carbon atoms as the monosaccharidic unit of the starting carbohydrate, for example, the preparation of sorbitol from a hexose. The starting carbohydrate may be converted to a polyhydric alcohol containing the same number of carbon atoms as the monosaccharidic unit of the starting carbohydrate at temperatures up to about 180°C. At temperatures above about 180°C., cracking of the carbon to carbon bonds starts to occur, and the amount of cracking increases as the temperature increases until, at a temperature of about 200°C., the product is predominantly a polyhydric alcohol containing a lower number of carbon atoms than monosaccharidic unit of the starting carbohydrate. Substantial cracking of carbon to carbon double bonds may be inducted at temperatures as low as about 180°C. by carrying the reaction out in the presence of a conventional cracking agent, such as lime. Thus, at temperatures of about 180°C., the carbon chain length of the resulting polyhydric alcohol product would depend upon whether the reaction is carried out in the presence or absence of a cracking agent. In general, the reaction is carried out at a temperature from about 120°C. to about 180°C., and preferably from about 140°C. to about 180°C., when the desired product is a polyhydric alcohol containing the same number of carbon atoms as the monosaccharidic unit of the starting carbohydrate; and the reaction is carried out at a temperature from about 180°C. to about 250°C., and preferably from about 210°C. to about 235°C., when the desired product is a polyhydric alcohol containing a lower number of carbon atoms than the monosaccharidic unit of the starting carbohydrate.

The time of reaction will depend upon the specific carbohydrate or carbohydrates being acted upon, the specific catalysts used, hydrogen pressure, temperature, and the concentration of the carbohydrate. Generally, the time may be from about 15 minutes to several hours and preferably from about 30 minutes to about 150 minutes. However, some reactions may take longer or shorter periods of time; and, in any event, the reactions should be continued until the hydrogenation or hydrogenolysis has been completed.

The reactants may be added to the reaction chamber in any suitable manner or in any suitable order. It is preferred to add the catalyst to the aqueous solution or suspension of the carbohydrate and then add the hydrogen under pressure and commence heating the mixture to the desired temperature.

The reaction may be carried out in any suitable type of apparatus which enables intimate contact of the reactants and control of the operating conditions and which is resistant to the high pressures involved. The process may be carried out in batch, semi-continuous, or continuous operation.

Upon completion of the reaction, the catalyst is removed by filtration of decantation and the polyhydric alcohols may be separated from the filtrate by any suitable means, such as, filtration, washing, crystallization, solvent extraction, and evaporation.

In order that those skilled in the art may better understand how the present invention may be practiced, the following examples are given. These examples are set forth solely for the purpose of illustration and any specific enumeration of details contained therein should not be interpreted as expressing limitations of this invention. All parts and percentages are by weight unless otherwise stated.

EXAMPLE 1

40 grams of kieselguhr are added to a stirred solution of 178.4 grams of $Ni(NO_3)_2 \cdot 6H_2O$ and 3.82 grams of $Cu(NO_3)_2 \cdot 3H_2O$ dissolved in 200 ml of distilled water in a two-liter beaker. A milky suspension of $(NH_4)_2WO_4$ (prepared by mixing $H_2WO_4$ and excess $NH_4OH$ on a steam bath) containing 10.0 grams of tungsten and 180 ml of concentrated ammonium hydroxide is added dropwise from a buret to the well-stirred slurry over a 30 minute period at 80°C. The slurry is digested with stirring for 1 hour at 80°C. after which time the pH is 5.2. A solution of 60.2 grams of anhydrous sodium carbonate dissolved in 150 ml water is then added dropwise from a buret over a 30 minute period. The pH is 7.5. After 30 minutes digestion at 90°C., the pH is 7.1. The green catalyst is filtered hot, washed with 8 liters of hot distilled water, and dried under vacuum at 150°C. for 17 hours. The green catalyst assay, as determined by laboratory analysis, is 30.9% nickel, 1.26% copper, and 8.27% tungsten in the form of tungsten oxide. The dried green catalyst is ground to pass through a 200 mesh screen and then activated by passing a stream of hydrogen over it at 400°C. for 30 minutes.

EXAMPLE 2

65.0 grams of kieselguhr are added to a solution of 99.2 grams of $Ni(NO_3)_2 \cdot 6H_2O$ in 250 ml distilled water in a 2-liter breaker. A milky suspension of $(NH_4)_2WO_4$ (prepared by mixing 13.6 grams $H_2WO_4$ and 90 ml concentration $NH_4OH$ on a steam bath) containing 10.0 grams tungsten is added dropwise from a buret over a 30 minute period at 80°C. after which time the pH is 5.4. A solution of 28.6 grams anhydrous sodium carbonate dissolved in 200 ml water is then added dropwise from a buret over a 30 minute period. The pH is 7.4 after carbonate addition. After 30 minutes digestion at 90°C., the pH is 7.1. The green cake is filtered hot, washed with 8 liters of hot distilled water and 500 ml acetone and dried under vacuum at 150°C. for 2.0 hours. The dried green catalyst (98.9 grams) is ground to pass through a 200 mesh screen and then activated by passing a stream of hydrogen through it at 500°C. for 30 minutes. The catalyst assayed 16.8% nickel and 8.5% tungsten.

EXAMPLE 3

The procedure of Example 2 is repeated with the following change: 27.2 grams $H_2WO_4$ (20.0 grams tungsten) are dissolved in 90 ml concentration $NH_4OH$. The same quantities of nickel nitrate kieselguhr and sodium carbonate are used. The pH after addition of $(NH_4)_2WO_4$ is 7.0, after addition of sodium carbonate 7.7, after digestion at 90°C. for 30 minutes 6.7. Yield: 111.6 grams dried green catalyst (15.0% nickel, 14.0% tungsten).

EXAMPLE 4

The procedure of Example 2 is followed. The pH after $(NH_4)_2WO_4$ addition is 5.4, 7.3 after carbonate addition, and 6.3 after digestion. Yield: 112.2 grams (19.5% nickel, 8.5% tungsten).

EXAMPLE 5

The procedure of Example 2 is followed with the exception that 6.8 grams $H_2WO_4$ (5.0 grams tungsten) are dissolved in 90 ml concentration $NH_4OH$. The pH after $(NH_4)_2WO_4$ addition is 5.7, after carbonate addition is 8.0, after digestion 7.1. Yield: 101.2 grams green catalyst (16.9% nickel, 7.0% tungsten)

EXAMPLE 6

The procedure of Example 2 is followed with the exception that 3.4 grams $H_2WO_4$ (2.5 grams tungsten) are used. The pH after $C NH_4)_2WO_4$ addition is 5.5, after carbonate 7.9, after digestion 7.1. Yield: 95.2 grams green catalyst (17.2% nickel, 2.2% tungsten).

EXAMPLE 7

The procedure of Example 2 is followed with the exception that 5.1 grams $H_2WO_4$ (3.7 grams tungsten) are used. The pH after ammonium tungstate addition 5.5, after carbonate addition 7.9, after digestion 7.1. Yield: 96.1 grams green catalyst (17.2% nickel, 3.6% tungsten).

EXAMPLE 8

The procedure of Example 2 is followed with the following changes: 130 grams kieselguhr, 178.4 grams $Ni(NO_3)_2·6H_2O$, 13.6 grams $H_2WO_4$ (10.0 grams tungsten) and 57.2 grams $Na_2CO_3$ are used. The pH after $(NH_4)_2WO_4$ addition is 5.8, after carbonate addition it is 8.1, and after digestion it is 7.6. Yield: 201.4 grams green catalyst (16.9% nickel, 4.3% tungsten).

EXAMPLE 9

The procedure of Example 1 is followed with the exception that copper is omitted. The pH after $(NH_4)_2WO_4$ addition is 5.6, after carbonate addition 7.4, and after digestion 7.3. Yield: 108.8 grams green catalyst (31.6% nickel, 8.4% tungsten).

EXAMPLE 10

The procedure of Example 9 is followed. The pH after $(NH_4)_2WO_4$ addition is 5.5, 8.1 after carbonate addition, and 7.3 after digestion. The catalyst, prior to reduction at elevated temperature in the presence of hydrogen, contains 28.7% nickel and 8.6% tungsten in the form of tungsten oxide, based on the total weight of catalyst.

EXAMPLE 11

A water slurry of the reduced nickel-tungsten oxide-copper catalyst of Example 1 containing that quantity of catalyst equivalent to 2.0% nickel, based on sugar, is heated under 500 psig hydrogen pressure to 230°C. in a one-liter stainless steel autoclave agitated by a turbine rotating at 3500 rpm. When temperature equilibrium is obtained, 140 grams of an agueous solution of invert sugar, containing 100 grams sugar solids, is displaced into the antoclave from a steam lagged pressure vessel by 2000 psig hydrogen pressure. After mixing with the catalyst-water slurry, the sugar concentration is 50%. The displacement takes 5 seconds after which the autoclave recovers temperature equilibrium (230°C.) in 25 seconds. Hydrogen is rapidly consumed for a period of 10 minutes, after which a slow, further reaction occurs. The initial rapid pressure drop corresponds to the hydrogenolysis of the sugar charged. The slow, secondary reaction corresponds to the further hydrogenolysis of hexitols. After 15 minutes at 230°C., the product comprises 18.7% glycerine, 13.8% propylene glycol, 4.1% ethylene glycol and 0.07% sugar. The non-distillable residue consisted primarily of sorbitol with minor amounts of mannitol, other hexitols, anhydro hexitols, and residual sugar.

When a prior art catalyst equivalent to those described in U.S. Pat. No. 3,341,609 (containing 16.4% nickel, 0.81% iron, and 1.05% copper) is tested under the same conditions, the product contains 4.8% glycerine, 1.5% propylene glycol, 0.47% ethylene glycol, and 0.11% sugar.

EXAMPLE 12

Example 11 is repeated except that sucrose is employed as feed material in place of the invert sugar. The product contains 19.4% glycerine, 13.5% propylene glycol, 2.5% ethylene glycol, and 0.08% sugar.

EXAMPLE 13

Example 12 is repeated with the exception that 0.5% of calcium oxide, based on the weight of sucrose, is added after 15 minutes at 230°C. The reaction is continued for 30 minutes at 230°C. The product, after ion exchange, contains 25.5% glycerine, 13.0% propylene glycol, 4.95% ethylene glycol, and 0.05% sugar.

In the following examples a water slurry of the indicated kieselguhr supported reduced nickel catalyst is heated under 500 psig hydrogen pressure to 180°C. in a one-liter stainless steel autoclave agitated by a turbine rotating at 3500 rpm. When temperature equilibrium is obtained, 140 gram charge of invert sugar, containing calcium hydroxide and 100 grams of sugar solids, is displaced into the autoclave from a steam lagged pressure vessel by 2000 psig hydrogen pressure. After mixing with the catalyst-water slurry, the sugar concentration is 50%. The displacement takes 5 seconds after which the autoclave recovers temperature equalibrium (180°C. in 25 seconds). Hydrogen is rapidly consumed for a period of 3 to 10 minutes, dependent upon the nickel to sugar ratio, after which a slow, further reaction occurs. The initial rapid pressure drop corresponds to the hydrogenolysis of the sugar charged. The slow, secondary reaction corresponds to the further hydrogenolysis of hexitols. After 30 minutes at 180°C. the product is removed from the autoclave and analyzed for glycerine. The glycerine content of the reaction product is shown in Table I. Numbered examples are in accordance with the process of this invention, and lettered examples are shown for purposes of comparison.

TABLE I

| Example Number | Catalyst of Ex. No. | Catalyst Concentration | Lime Concentration | Glycerine |
|---|---|---|---|---|
| A | (a) | 2.0% | 0.50% | 14.6 |
| B | (b) | 2.0% | 0.50% | 15.0 |
| 14 | 2 | 2.0% | 0.50% | 21.8 |
| 15 | 3 | 2.0% | 0.50% | 19.4 |
| 16 | 4 | 2.0% | 0.50% | 21.2 |
| 17 | 5 | 2.0% | 0.50% | 24.4 |
| 18 | 6 | 3.0% | 1.0% | 24.7 |
| 19 | 7 | 3.0% | 1.0% | 24.9 |
| 20 | 8 | 3.0% | 1.0% | 25.2 |

(a) Kieselguhr supported reduced nickel catalyst prepared according to the procedure of U.S. Pat. No. 3,341,609 and containing 20% nickel, 0.8% iron, 0.5% copper, and 0% tungsten.
(b) Kieselguhr supported reduced nickel catalyst prepared according to the procedure of U.S. Pat. No. 3,341,609 and containing 21.6% nickel, 0.9% iron, 3.3% copper, and 0% tungsten.

EXAMPLE 21

Example 11 is repeated with the exception that the catalyst used is the reduced catalyst of Example 9. The product contains 19.7% glycerine, 14.2% propylene glycol, 2.58% ethylene glycol, and 0.07% reducing sugar.

EXAMPLE 22

Example 21 is followed with the exceptions that the temperature is 210°C. and the reaction time is 30 minutes. The product contains 14.1% glycerine, 6.4% propylene glycol, and 0.71% ethylene glycol.

EXAMPLE 23

The procedure of Example 22 is followed with the exceptions that the temperature is 200°C. and the nickel-sugar-ratio is 1.0% instead of 2.0%. The product contains 13.4% glycerine, 7.6% propylene glycol and 0.61% ethylene glycol.

EXAMPLE 24

A water slurry of the reduced nickel-tungsten oxide catalyst of Example 10 containing that quantity of catalyst equivalent to 2.0% nickel, based on sugar, is heated under 500 psig hydrogen pressure to 160°C. in a one-liter stainless steel autoclave agitated by a turbine rotating at 3500 rpm. At 160°C., a 140 gram charge of invert sugar containing 100 grams of sugar solids is charged into the autoclave from a steam lagged pressure vessel by 2000 psig hydrogen pressure. After 30 minutes at 160°C., the product contains 26.7% mannitol, 71.3% sorbitol, 0.05% reducing sugar, and 0.17% non-reducing sugar.

EXAMPLE 25

Example 24 is repeated with the exceptions that the catalyst employed is the catalyst of Example 1 and that the amount of catalyst is such as to furnish 1.0% nickel, based on the weight of sugar. After 30 minutes at 160°C., the product contains 68.3% sorbitol, 27.2% mannitol, 0.09% reducing sugar, and 0.25% non-reducing sugar.

EXAMPLE 26

Example 24 is repeated with the exception that sucrose is used in place of invert sugar. After 30 minutes at 160°C. the product contains 70.0% sorbitol, 28.4% mannitol, and 0.44% non-reducing sugar.

EXAMPLE 27

Hydrogenation of a quantity of corn starch hydrolyzate containing 100 grams of sugar solids and 3% nickel catalyst based on the weight of sugar is conducted in a two-stage process at 160°–180°C. The catalyst employed is the reduced catalyst of Example 10. The corn starch hydrolyzate used is a hydrolysis product of corn starch and contains about 63% dextrose, about 17% disaccharide, about 4% trisaccharide, about 3% tetrasaccharides, and about 12% higher polysaccharides. The reaction was conducted at about 160°C. and 2000 psig hydrogen pressure for 30 minutes, and then at 180°C. for 2 hours. The product contains 93.0% sorbitol, 1.3% mannitol, 1.54% hexitan, 0.04% reducing sugar, and 0.25% non-reducing sugar.

EXAMPLE 28

An aqueous solution of corn starch hydrolyzate having a dextrose equivalent of 77.5 is slurried with a catalyst consisting of finely divided metallic nickel and finely divided tungsten oxide supported on kieselguhr wherein the metallic nickel content is 41% by weight of catalyst and the tungsten content is 8% by weight of catalyst. The slurry contains 50% by weight of sugar solids based on the weight of the slurry and 1.7% catalyst based on the weight of sugar. Successive batches of this slurry are pumped at a rate of 20 liters per hour to a system of five autoclaves connected in series. The pressure on all five autoclaves is maintained at 2000 psig of hydrogen, and the slurry is agitated by the addition of high pressure hydrogen. The temperature in the first autoclave is maintained at 160°C., 170°C. in the second autoclave, and 174°C. in each of the remaining three autoclaves. The product of the fifth reactor is filtered and ion exchanged. The product contains, based on the weight of solids, 94% sorbitol and 0% iditol.

EXAMPLE 29

An aqueous solution of invert sugar is slurried with a catalyst consisting of finely divided metallic nickel and finely divided tungsten oxide supported on kieselguhr wherein the metallic nickel content is 31% by weight and the tungsten content is 10% by weight, based on the total weight of catalyst. The slurry contains 50% by weight of sugar based on the weight of slurry and 1.7% by weight of metallic nickel based on the weight of sugar. Successive batches of this slurry is pumped at a rate of 8.3 liters per hour to a system of four autoclaves connected in series. The volume of each autoclave is 8.7 liters. In all four autoclaves, the pressure is maintained at 2000 psig of hydrogen and the temperature at 220°C. The product of the fourth autoclave contains 32.6% glycerine.

EXAMPLE 30

The process of Example 29 is repeated with the exception that 0.5% by weight of lime, based on the weight of invert sugar, is added to the feed slurry. The product of the fourth reactor contains 34.7% glycerine.

Although this invention has been described with reference to specific carbohydrates and catalysts and to specific reaction conditions, it will be appreciated that numerous other carbohydrates and catalysts may be substituted for those specifically described and that the particular reaction conditions employed may be modified, all within the spirit and scope of this invention as defined in the appended claims.

Having described the invention, what is desired to be secured by Letters Patent is:

1. A process for the preparation of glycerin from polysaccharide which consists essentially of contacting an aqueous solution of polysaccharide containing from 20% to about 80% by weight of dissolved polysaccharide with hydrogen at a pressure between about 70 atmospheres and about 150 atmospheres, at a temperature from about 180°C to about 250°C and in the presence of a supported nickel catalyst consisting essentially of finely divided metallic nickel and finely divided tungsten oxide supported on an inert carrier wherein the nickel content is from 5% to 45% by weight based on the total weight of nickel, tungsten oxide, and inert carrier and the amount of tungsten in the form of tungsten oxide is from 0.5% to 16% by weight based on the total weight of metallic nickel, tungsten oxide, and inert carrier.

2. A process of claim 1 wherein the polysaccharide is sucrose.

3. A process of claim 1 wherein the polysaccharide is a cornstarch hydrolyzate.

4. A process of claim 1 wherein the catalyst is a precipitated catalyst of finely divided metallic nickel, finely divided tungsten oxide, and finely divided iron supported on an inert carrier wherein the nickel content is from 15% to 45% by weight based on the total weight of catalyst, the tungsten content is from 0.5% to 16% by weight, based on the total weight of catalyst and the amount of iron present in the catalyst is not more than 2.5% by weight, based on the total weight of catalyst.

5. A process of claim 1 wherein the weight percent of nickel is from 18% to 25% by weight and the weight percent of tungsten is from 2% to 25% by weight.

6. A process of claim 1 wherein the catalyst is prepared by forming a slurry of an inert carrier in an acidic, aqueous solution of nickel nitrate and ammonium tungstate, neutralizing the slurry with an alkali metal carbonate to precipitate nickel carbonate, nickel hydroxide, and tungsten oxide onto the surface of inert carrier, and reducing the nickel carbonate and nickel hydroxide to metallic nickel.

7. A process of claim 1 wherein the temperature is from 210° to 235°C.

8. A process of claim 7 wherein the polysaccharide is sucrose.

* * * * *

UNITED STATES PATENT AND TRADEMARK OFFICE
CERTIFICATE OF CORRECTION

PATENT NO. : 3,965,199
DATED : June 22, 1976
INVENTOR(S) : Leon W. Wright

It is certified that error appears in the above-identified patent and that said Letters Patent are hereby corrected as shown below:

Column 6, line 19, "filtration of decantation" should read -- filtration or decantation --.

Column 6, line 59, "99.2 grams" should read -- 89.2 grams --.

Column 7, line 38, "CNH$_4$)$_2$WO$_4$" should read -- (NH$_4$)$_2$WO$_4$ --.

Column 8, line 14, "agueous" should read -- aqueous --.

Column 8, line 16, "antoclave" should read -- autoclave --.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks